US008317688B2

(12) United States Patent
Glozman et al.

(10) Patent No.: US 8,317,688 B2
(45) Date of Patent: Nov. 27, 2012

(54) MULTI-VIEW ENDOSCOPIC IMAGING SYSTEM

(75) Inventors: Daniel Glozman, Kfar Adummim (IL); Noam Hassidov, Bustan Hagalil (IL); Moshe Shoham, Hoshaya (IL)

(73) Assignee: Technion Research & Development Foundation Ltd., Technion, Haifa (IL)

( * ) Notice: Subject to any disclaimer, the term of this patent is extended or adjusted under 35 U.S.C. 154(b) by 384 days.

(21) Appl. No.: 12/739,746

(22) PCT Filed: Oct. 26, 2008

(86) PCT No.: PCT/IL2008/001413
§ 371 (c)(1),
(2), (4) Date: Apr. 26, 2010

(87) PCT Pub. No.: WO2009/053989
PCT Pub. Date: Apr. 30, 2009

(65) Prior Publication Data
US 2011/0196200 A1 Aug. 11, 2011

Related U.S. Application Data

(60) Provisional application No. 60/996,008, filed on Oct. 24, 2007.

(51) Int. Cl.
*A61B 1/06* (2006.01)
(52) U.S. Cl. ..................................... 600/173
(58) Field of Classification Search ............ 600/160, 600/173
See application file for complete search history.

(56) References Cited

U.S. PATENT DOCUMENTS

| 4,467,361 | A | 8/1984 | Ohno et al. | |
|---|---|---|---|---|
| 5,709,653 | A | 1/1998 | Leone | |
| 6,154,586 | A | 11/2000 | MacDonald et al. | |
| 6,577,891 | B1 | 6/2003 | Jaross et al. | |
| 6,736,773 | B2 | 5/2004 | Wendlandt et al. | |
| 2003/0174208 | A1 | 9/2003 | Glukhovsky et al. | |
| 2004/0254424 | A1* | 12/2004 | Simkulet et al. | 600/176 |
| 2006/0184039 | A1 | 8/2006 | Avni et al. | |
| 2006/0217593 | A1* | 9/2006 | Gilad et al. | 600/160 |
| 2008/0045797 | A1* | 2/2008 | Yasushi et al. | 600/175 |

\* cited by examiner

*Primary Examiner* — Clayton E Laballe
*Assistant Examiner* — Noam Reisner
(74) *Attorney, Agent, or Firm* — Daniel J. Swirsky; AlphaPatent Associates Ltd.

(57) ABSTRACT

Endoscopic illumination and imaging systems for enabling observation of both the forward and rearward directions in a lumen using only a single imaging device. According to one implementation, the system utilizes the effects of a partially reflective mirror to respectively transmit and reflect light from the different portions of the lumen or cavity, and uses separate groups of illumination sources to illuminate one or the other section of the lumen, such that the illuminated section is preferentially imaged by virtue of its increased light level. In a second implementation, electrically switched mirrors are used, having properties switched between a transmissive and a partially reflective state, such that the mirror can be switched between imaging the regions forward of the camera when in a transmissive state, and imaging the regions rearward of the camera when in a reflective state. A mechanically swiveled mirror is described for the same purpose.

5 Claims, 12 Drawing Sheets

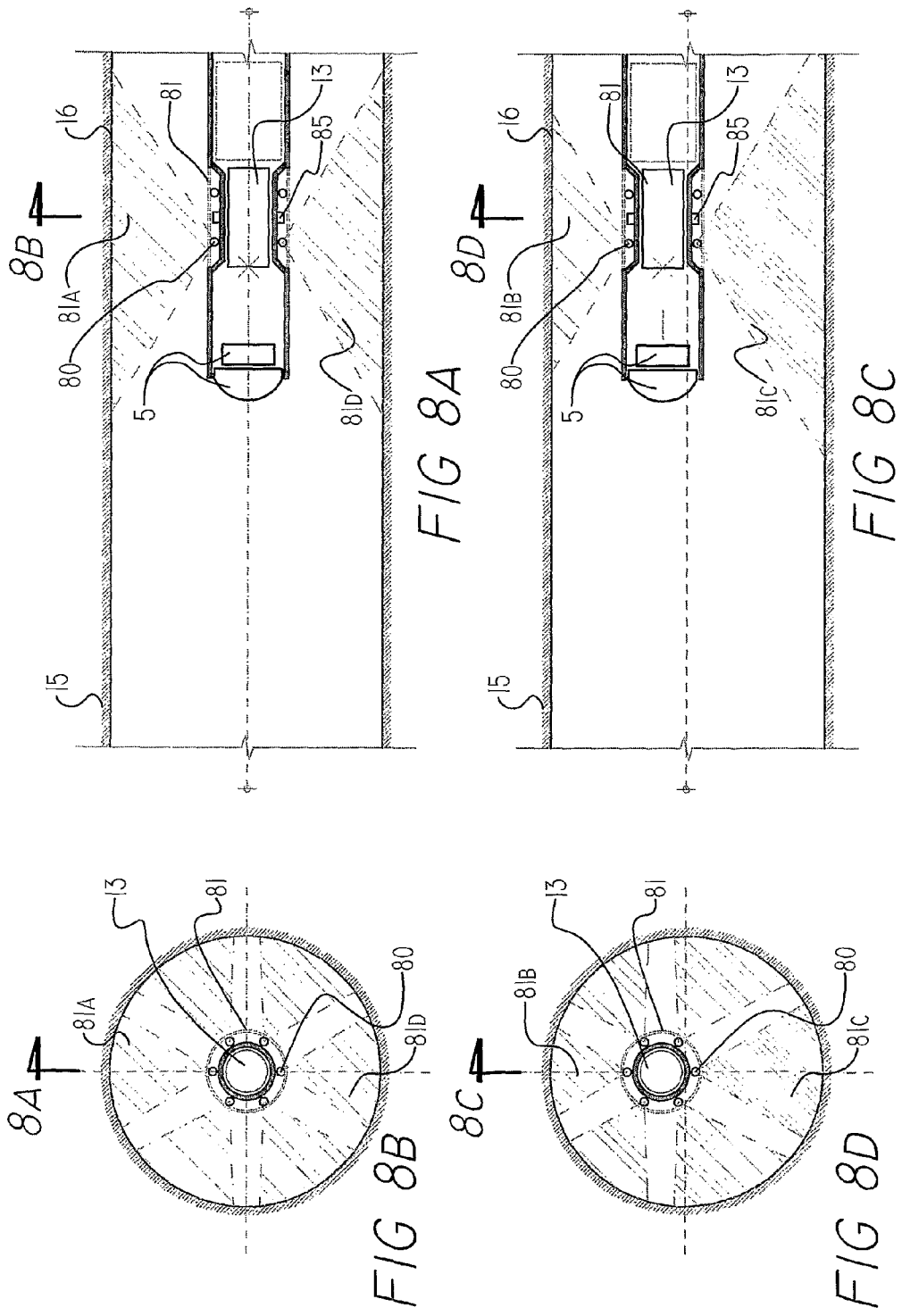

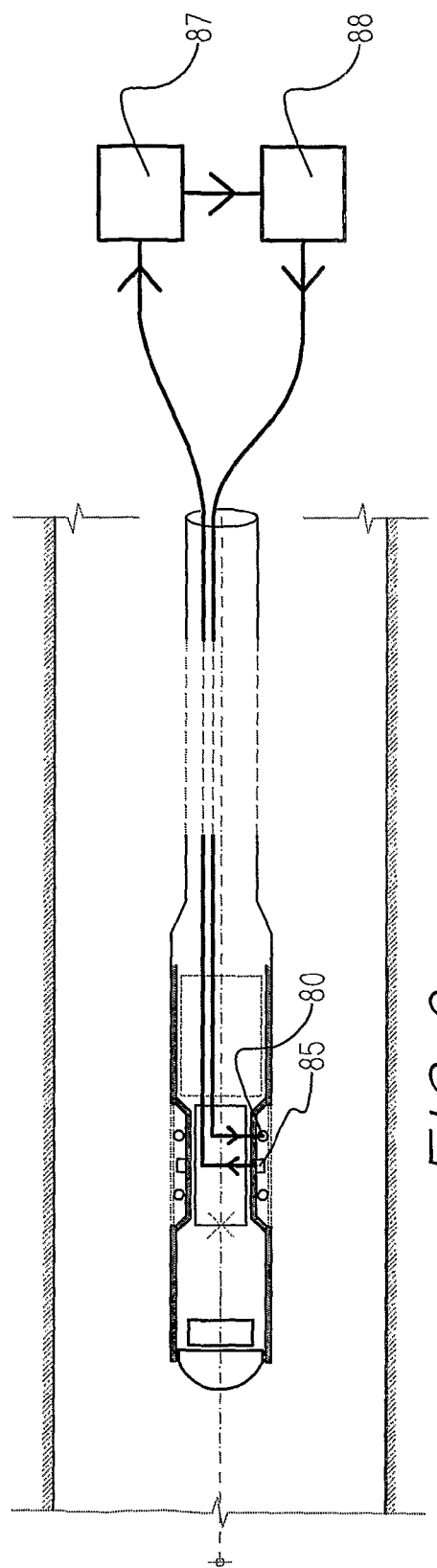

MULTI-VIEW ENDOSCOPIC IMAGING SYSTEM

CROSS-REFERENCE TO RELATED APPLICATIONS

This application is a U.S. National Phase Application under 35 U.S.C. 371 of PCT International Application No. PCT/IL2008/001413, which has an international filing date of Oct. 26, 2008, and which claims priority benefit from U.S. Provisional Patent Application No. 60/996,008, filed Oct. 24, 2007, the contents of which are herein incorporated by reference in their entirety.

FIELD OF THE INVENTION

The present invention relates to the field of imaging devices for use in lumens, capable of viewing in multiple directions, especially for endoscopic use.

BACKGROUND OF THE INVENTION

Conventional endoscopes generally provide only a forward field of view. The field of view angle changes from endoscope to endoscope and can differ from narrow angle to a wide 170° field of view. The geometry of inspected medical and non-medical lumens is usually very complex and it would be useful to have the ability to image over a much wider field of view, and especially to look backwards. Numerous endoscopes provide steering capability where the operator can steer the endoscope tip in order to see and diagnose the surrounding tissue Unfortunately the lumen traversed is usually narrow and the endoscope tip radius of curvature is larger then the lumen diameter so it is not generally possible with current endoscopes to steer back and look backwards, and if possible, such a maneuver may be painful for the patient and might cause damage to the lumen tissue.

Several solutions have been suggested in the prior art for enhancing the backward view, but there exist a number of drawbacks, such as the need for moving parts which may be difficult to implement in a small endoscope, or which do not deliver the full surround view. Examples of systems for generating views of the internal surfaces of a lumen include the GI-View OmniView camera that is said to deliver a 270° field of view, as described in the article "The Aer-O-Scope: Proof of Concept of a Pneumatic, Skill-Independent, Self-Propelling, Self-Navigating Colonoscope in a Pig Model," by Pfeffer et al., published in Endoscopy, Vol. 38, pages 105-208 (2006). Another example of such a system is given in International Patent Application Publication No. WO 2006/129977, for "Method and device for simultaneously outputting images of internal front and lateral sides of a pipe".

Another example is shown in U.S. Pat. No. 4,846,154, which describes two imaging lenses oriented at different angles, and a plate that controls passage or reflection of light through it, controlling from which lens the light is imaged.

The disclosures of each of the publications mentioned in this section and in other sections of the specification are hereby incorporated by reference, each in its entirety.

SUMMARY OF THE INVENTION

The present disclosure describes endoscopic illumination and imaging systems and methods for enabling observation of both the forward and rearward directions in a lumen or cavity, whether simultaneously or sequentially, using only a single imaging device. According to one implementation, the system utilizes the effects of a partially reflective mirror to respectively transmit and reflect light from the different portions of the internal lumen or cavity, and uses separate groups of illumination sources to illuminate one or the other section of the lumen or cavity, such that the illuminated section is preferentially imaged by virtue of its increased light level. Methods are described of eliminating the spurious weak images obtained when light from the illuminated section reaches the non-illuminated section and is imaged from there. Such methods use signal processing manipulation of the images obtained.

According to other exemplary systems described in this disclosure, electrically switched mirrors are used, which can have their properties switched between a transmissive or partly transmissive state and a partially reflective state, such that the mirror can be switched on-demand between imaging the regions forward of the mirror and camera when in a transmissive state, and imaging the regions rearward of the mirror and camera when in a reflective state. Such an implementation does not require separately activated illumination sources, but can rely on uniform internal illumination, or even on ambient illumination where relevant.

Similar imaging effects can be obtained using another exemplary system in which the mirror is switched between a reflective or transmissive function by the simple mechanical expediency of swinging it into or out of the line of sight of the camera. When in position, it reflects the rearward view into the camera lens; when swung out of position, the camera images only the forward view of the lumen. In such an instrument, the mirror can be full reflective for increased optical performance.

A further mechanical arrangement for achieving such double viewing capabilities is obtained in another exemplary endoscope head, in which the rear view mirror has a viewing aperture at its center, and is arranged to be linearly moveable relative to the camera. When the camera and mirror are close together, the camera images the forward view through the mirror aperture. When the camera and mirror are separated, the camera images the rearward view by reflection of that view in the mirror. The camera can be fixed and the mirror moveable, or alternatively, the mirror can be fixed and the camera moveable, or both can be moveable, though that arrangement is mechanically more complex.

Another exemplary system uses a single convex mirror positioned in front of the camera, in combination with a ring-shaped mirror positioned proximally to it. The convex mirror reflects the light coming from the rear of the camera into the camera, to generate the rear view. The ring mirror collects light from the front section of the lumen, and reflects it back into the convex mirror from where it is again reflected into the camera to generate the forward view. Since the focusing power of the convex mirror needs to be different when handling light directly from the rear part of the lumen, from that required when handling light from the front part of the lumen after reflection in the ring mirror, especially when the ring mirror does not have a planar surface, the parts of the convex mirror handling each of these views should have different radii of curvature, to perform their different focusing functions. Therefore, the central part of the convex mirror should have a different radius of curvature, or more generally, a different optical power, from the peripheral part of the mirror.

Another described system, useable for any type of endoscope, whether double view or not, provides compensation for the changes in image intensity generated by motion of the endoscope head off the center line of the lumen, with the consequent change in the luminous intensity falling on the various circumferential parts of the lumen wall. The illumination sources spaced around the endoscope head are separately driven such that their illumination level can be separately varied to compensate for the increase or decrease of the wall illumination according to the closeness of the head to the wall. Automatic control systems for providing constant wall illumination are also described.

A further exemplary implementation of an endoscopic illumination system providing dual direction imaging uses a rear view mirror in the form of an inflatable reflective balloon. The balloon can be passed through the endoscope working channel and inflated when fully deployed ahead of the camera. Reflection of the light coming from rearward of the camera in the inflated reflective balloon enables this rear light to be imaged by the camera. The forward view is imaged by the camera in the usual manner, with the balloon either deflated or withdrawn to its undeployed position.

There is also provided in accordance with an exemplary system according to the presently claimed invention, a a system for viewing the inside surface of a lumen, the system comprising:
(i) an imaging device directed along the lumen,
(ii) a partially reflective mirror disposed distal to the imaging device such that it reflects into the imaging device light from the inside surface of the lumen proximal to the mirror, and transmits into the imaging device light from the inside surface of the lumen distal to the mirror,
(iii) a first illuminating system for illuminating the inside surface of the lumen proximally to the partially reflecting mirror, and
(iv) a second illuminating system for illuminating the inside surface of the lumen distally to the partially reflecting mirror, wherein the first illuminating system and the second illuminating system can be separately activated, such that images of the inside surface of the lumen proximally and distally to the mirror can be obtained with the imaging device.

In the above described system, the imaging device may be synchronized with the activation of the illuminating systems such that the inside surface of the lumen can be viewed both distally and proximally to the partially reflecting mirror.

The system may further comprise an image processing unit which subtracts a processed first image of the inside surface of the lumen proximal to the mirror obtained when the first illuminating system is activated, from a second image of the inside surface of the lumen distal to the mirror obtained when the second illuminating system is activated, such that spurious effects in the second image arising from illumination of the lumen proximal to the mirror by light from the second illumination system, is reduced.

Alternatively, the system may further comprise an image processing unit which subtracts a processed first image of the inside surface of the lumen distal to the mirror obtained when the second illuminating system is activated, from a second image of the inside surface of the lumen proximal to the mirror obtained when the first illuminating system is activated, such that spurious effects in the second image arising from illumination of the lumen distal to the mirror by light from the first illumination system, is reduced.

In any of the above described systems, the first illuminating system and the second illuminating system may be activated alternately at such a rate that a composite image of the inside surfaces of the lumen proximal and distal to the mirror may be obtained. Furthermore, in any of the above described systems, the partially reflective mirror may advantageously be a convex mirror.

A further exemplary system for viewing the inside surface of a lumen comprises:
(i) an imaging device directed along the lumen, and
(ii) a mirror, constructive and operative to have either a reflective or a transmissive status, the mirror being disposed distal to the imaging device such when in its reflective status, it reflects into the imaging device light from the inside surface of the lumen proximal to the mirror, and when in its transmissive status, it transmits into the imaging device light from the inside surface of the lumen distal to the mirror.

In such a system, the mirror may be electrically switchable between the reflective and transmissive statuses, or it may be switchable between the reflective and transmissive statuses by virtue of its mechanical position relative to the imaging device. Alternatively, the mirror may have a transparent shell incorporating a hollow internal cavity, the mirror being switchable between the reflective and transmissive statuses by virtue of the introduction of a reflective fluid into the cavity. In any of these systems, the mirror may advantageously be a convex mirror.

Other implementations described in this disclosure may involve a system for viewing the inside surface of a lumen, the system comprising:
(i) an imaging device directed along the lumen, and
(ii) a mirror disposed distal to the imaging device, the mirror comprising a central aperture, and being mutually movable in a direction along the lumen, such that when the imaging device is disposed at a predetermined distance from the mirror, the imaging device images the inside surface of the lumen proximal to the mirror, and when the imaging device is disposed close to the mirror, the imaging device images, through the aperture, the inside surface of the lumen distal to the mirror.

In such a system, either the imaging device may be moveable relative to a static mirror, or the mirror may be moveable relative to a static imaging device, or both mirror and imaging device may be moveable. The mirror may advantageously be a convex mirror.

Additional exemplary implementations can include a system for viewing the inside surface of a lumen, the system comprising:
(i) an imaging device directed along the lumen,
(ii) a first mirror disposed distal to the imaging device, such that it reflects into the imaging device light from the inside surface of the lumen proximal to the first mirror, and
(iii) a second mirror having a ring shape, disposed proximal to the first mirror, and with its reflecting surface directed in a distal direction such that it reflects into the first mirror light from the inside surface of the lumen proximal to the first mirror, which light the first mirror then reflects into the imaging device.

In these implementations, the second mirror having a ring shape ring may have either one of a concave, planar or convex surface. Additionally, the diameter of the first mirror should be sufficiently small that the first mirror does not obstruct light which it is desired to image coming from the furthest sections of the inside surface of the lumen distal to the system, from impinging on the second ring mirror. Furthermore, the first mirror may have two concentric regions of different radii of curvature, such that the first mirror can separately direct into the imaging device, the light coming directly from the inside surface of the lumen proximal to the first mirror, and the light coming from the inside surface of the lumen distal to the first mirror after reflection in the second mirror. The first mirror may advantageously have a convex surface.

Another example implementation can involve a head for illuminating the inside surfaces of a lumen, the head comprising a plurality of illumination sources directed towards the inside surfaces of the lumen, the sources being arranged around the head at different angular locations, wherein the power supplied to at least some of the sources can be varied in accordance with the radial position of the head within the lumen, such that the uniformity of illumination on the inside surfaces of the lumen can be maintained independently of the radial position of the head within the lumen.

In such an exemplary head implementation, the power supplied to at least some of the sources may be varied in accordance with the angular distribution of the illumination intensity obtained on an image of the inside surfaces of the lumen.

Such a head may further comprise a plurality of luminous intensity detectors also arranged around the head at different angular locations, the luminous intensity detectors providing an indication of the angular distribution of the illumination on the inside surfaces of the lumen.

Any of the above described heads may further comprise a control system which varies the power supplied to at least some of the sources in accordance with the angular distribution of the illumination intensity on the inside surfaces of the lumen. In such a case, the control system may be adapted to receive information from the luminous intensity detectors regarding the angular distribution of the illumination intensity on the inside surfaces of the lumen.

A further exemplary endoscopic head for viewing the internal walls of a lumen may be described comprising:
(i) an imaging device and a working channel adjacent thereto, and
(ii) an inflatable balloon attached to an inflation tube threaded through the working channel,
wherein the inflatable balloon may be constructed of an optically reflective material, such that when the balloon is projected from the distal end of the working channel and inflated, it reflects images of the internal walls of the lumen proximal to the balloon into the imaging device.

In such a head, images of the internal walls of the lumen distal to the endoscopic head may be imaged directly by the imaging device.

Although the various examples described in this application relate to an endoscope, as generally used for bodily use, it is to be understood that this application is not intended to be limited to such use, but may include systems for the visual inspection of any sort of lumen or internal passageway or even a cavity, whether in the medical or industrial field.

Furthermore, the location of the parts of the inside surfaces of the lumen are generally described and claimed as being forward or rearward relative to the main reflection mirror of the systems described, though it is to be understood that this is also generally equivalent to their positions relative to the systems described, and relative to the imaging device. The terms forward and rearward are used to mean relative to the direction in which the imaging device or the endoscope is orientated within the lumen, which is the direction in which the imaging device or endoscope is inserted into the lumen. Additionally, the terms distal and proximal are used in their conventional terminological sense, namely that the direction away from the insertion point of the endoscope is termed the distal direction (i.e. the forward direction), and the direction towards the insertion point of the endoscope is termed the proximal direction (i.e. the rearward direction).

BRIEF DESCRIPTION OF THE DRAWINGS

The present claimed invention will be understood and appreciated more fully from the following detailed description, taken in conjunction with the drawings in which:

FIGS. 8A to 8E illustrate an endoscope system equipped with multiple illumination sources arranged around the periphery of the endoscope head, and a control system for ensuring uniform lumen illumination despite endoscope motion off the lumen centerline.

DETAILED DESCRIPTION

Figure 1A:
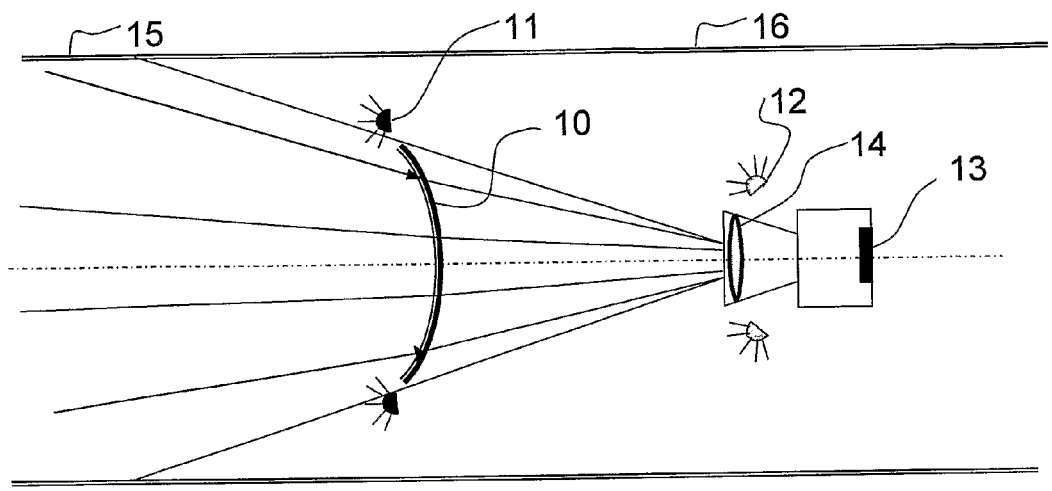
FIGS. 1A and 1B illustrate schematically an exemplary endoscopic multi-view camera system, which operates using illumination switching.
Figure 1B:
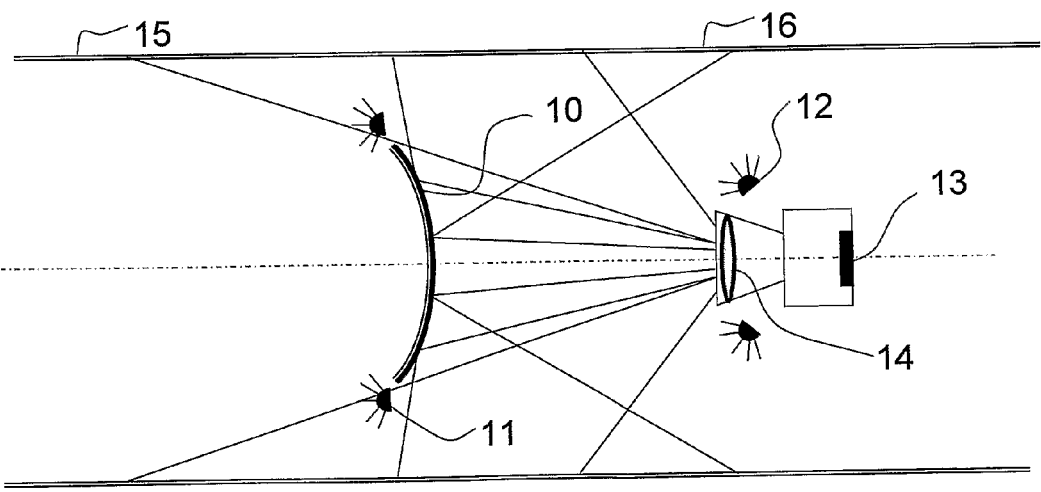

Reference is now made to FIGS. 1A and 1B, which illustrate schematically an exemplary endoscopic multi-view camera system, which operates using illumination switching to illuminate separate sections of a lumen into which the endoscope is inserted. The device preferably comprises a forward looking camera 13 having an imaging lens 14 which should provide a wide field of view for most convenient ease of use, a field of view of at least 70° being advisable. The camera may be understood to include a pixilated digital sensor, such as a CCD or CMOS array, and an optical system delivering the image onto the sensor. Alternatively a fiber optic camera system may be used, in which a fiber optical system delivers the image to a remote camera. The camera may also incorporate image processing software modules, or these may be incorporated in a separate computing device located external to the endoscope, as is known in the art.

In front of the camera, a partially reflective mirror 10 may be disposed, the mirror partially reflecting and partially transmitting light incident on it. A double illumination system should be provided for the purpose of delivering light to the surrounding tissue, either by means of one or more optic fibers from an external light source or sources, or by means of Light Emitting Diodes (LED's) located in the vicinity of the imaging system.

The double illuminating system should have its illuminating sources arranged in two groups, one of which is responsible for providing illumination in the general region from the camera and in a forward direction, and the other in the general region from the camera in a reverse direction. The terms forward and reverse are understood in this application to refer to the distal and proximal directions within the lumen in which the endoscope is inserted, relative to the position of the camera at the distal end of the endoscope. FIG. 1A shows the situation when only the front illumination is active, by LED's 11. Light reflected from the tissue of the inner wall of the lumen 15 forward of the camera, impinges on the partially reflective mirror 10, such that part of it is reflected back towards the distal part of the lumen, and part of it traverses the partially reflective mirror 10 and is imaged by the camera 13. Since the backward directed illumination provided by the rearward disposed LED's 12 is not active, virtually no light enters the camera from the rear view, such that an image of frontal tissue only is obtained.

On the other hand, as shown in FIG. 1B, when only the backward illumination is present, by activation of the rearward directed LED's 12, the rearward located tissue 16 is illuminated and light that is reflected therefrom impinges on the partially reflective mirror 10. Part of that light passes through and is dispersed onto the distal regions of the lumen wall, and part of it is reflected from the mirror 10 into the camera 13. The front illumination is not active, so that the only light originating from the distal regions 15 of the lumen wall is from that part of the reflected light from the proximal regions of the lumen wall, transmitted by the partially reflective mirror 10. Since this light is divergent, it should not illuminate the front region of the lumen with sufficient intensity to significantly interfere with the imaging of the strongly illuminated and converged light from the proximal wall regions 16. Thus the camera essentially receives only the backward images that are strongly illuminated by the backward directed light. A method is described hereinbelow, by which it becomes possible to reduce the effect of this small residual parasitic illumination.

The partially reflective mirror 10 preferably has a rearward shaped convex surface. Use of such a surface will enhance the ability of the system to image as large a field of view as possible, since it enables the mirror to collect light coming from the walls of the lumen essentially level with the mirror, and even beyond. Such convex mirrors are shown in most of the exemplary systems described in this application. It is however to be understood that this is not meant to be a limitation of the systems shown in this disclosure, but is merely the most versatile implementation from the point of view of the extent of lumen wall covered by the imaging device. Planar or even concave mirrors can also be used, but such mirrors would not generally enable imaging of the regions opposite the imaging device, and would not enable overlapping images of forward and rearward directions to be obtained.

Using the above-described light switching technique, it is possible to switch between viewing directions very quickly, since no mechanical movement or steering of the endoscope is required to change the viewing direction. The switching speed is limited only by the response time of the illumination sources. In the case of LED's, the response time is of the order of milliseconds. All that is required is to switch intermittently between the frontal and backward lighting, preferably at about 50 times a second, thus allowing the capture of both frontal and backward images at the rate of 25 frames per second. Using image de-warping and image stitching software incorporated into a signal processing unit, the frontal and backward images may be combined to obtain a live 360° image, apart from small dead spaces generated by the camera itself and by the obstructing front LED's.

When operating in a lumen or cavity, reflection and scatter from the tissue will occur. Thus when the system is in its front viewing mode, some of the illumination on the front walls 15 will be scattered to the back viewing field and illuminate the walls 16 of the back region. This will be particularly so if a projection from the front wall 15, such as a polyp, is encountered. In this case the mirror 10 will cause the camera 13 to image both the primary image front view (which may be typically the majority of the illumination, perhaps 80% or 90% or more, for example) and a much weaker reflected residual image back view (10% to 20% or less of the illumination, for the above example) from the spurious illumination falling on the rear walls 16. Although the illumination of the back region will be much lower than that of the front region, its presence will nevertheless degrade the front image.

The same effect occurs when the rear view image is being taken using rearward directed illumination, and part of that illumination from the rear walls 16 passes through the mirror and illuminates the front walls 15, generating in the camera also a weak front residual image.

In order to resolve this problem, a set of two images, one of the front view and one of the rear view may be taken as close together in time as possible, with the first image taken under front illumination and the second under back illumination. Because of the above-mentioned spurious illumination effects, each image will have 2 components—the first image, taken using front illumination only, will have a primary front view image and a residual weak back view image, while the second image taken using back illumination, will have a primary back view image and a residual weak front view image. When wishing to obtain a clear image of the front view, the image processing software of the system can then take the primary back view image, attenuate it to the level expected of the residual rear view image obtained when imaging the front view, and Boolean subtract that attenuated rear view image from the actual front view image to obtain a clearer front view image without the effects of the spurious back view image. Even if the endoscope or the lumen has moved slightly between the first and second images, (in those cases where the illumination cannot be switched at the desired 50 Hz rate or similar) the image processing software can compensate for such movement.

A similar process can be performed to obtain a clearer back view without interference from spurious light from the front view, by subtracting an attenuated front view image from the actual image obtained in the back view.

The example system shown hereinabove in FIGS. 1A and 1B utilizes switched sources to illuminate sequentially either the front or the rear sections of the lumen relative to the endoscope camera or relative to the mirror. According to other exemplary endoscopic illumination systems now to be described in this disclosure, it is possible to use unswitched illumination, whether ambient or applied by means of sources inserted into the lumen, with the switching between the front and rear views performed by manipulation of the imaging optics, rather than by switching illumination sources.

Figure 2A:
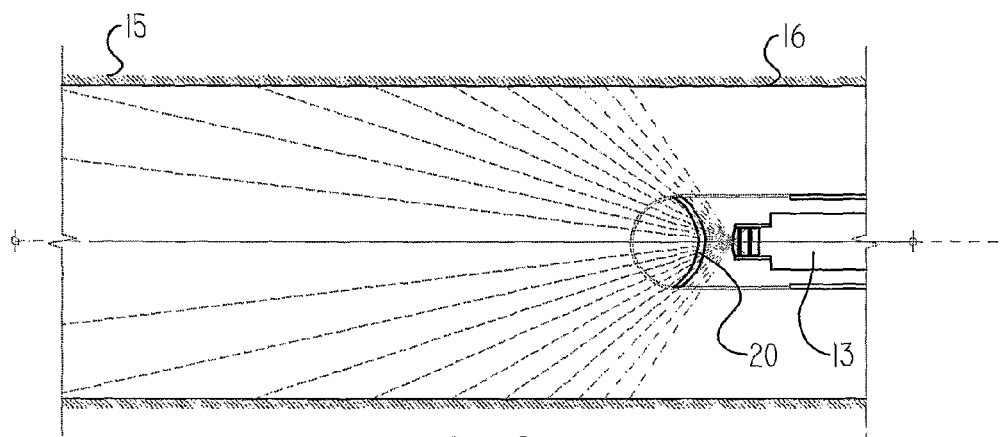
FIGS. 2A and 2B show a schematic endoscopic illumination system using an electrically switched mirror.
Figure 2B:
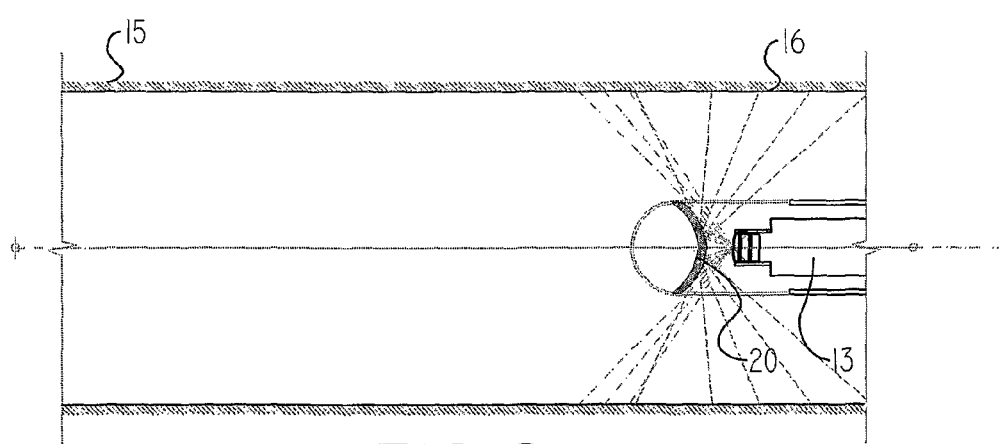

The first described of such systems is shown in FIGS. 2A and 2B, which show a schematic endoscopic illumination system using an electrically switched mirror. The mirror properties can be electrically switched from essentially transmissive to reflective. Since electrically switchable reflective materials are not generally available, though it is feasible that such materials may become generally available in the future, such an electrically switched mirror can be produced using materials which are switchable between essentially transparent and opaque states, by also incorporating a partially reflective coating on the outer layer. Such transparent/opaque switchable materials are readily available, such as in liquid crystal cells, or other cells having a polarizing element with an electrically variable polarization rotation element, or electrochromic layers such as the glasses supplied by Sage Electrochromics Inc. of Faribault, Minn., or any other electrochemical, physical, or other electrical technique which can modify the optical transmission of the medium. The reflectivity of the applied coating, or the natural reflection level of the outer layer if uncoated, determines the reflectivity of the mirror. When the material is switched to its essentially transparent status, light incident on its outer surface is partially transmitted, and partially reflected, depending on the reflectivity of the coating. When the material is switched to its essentially opaque status, light incident on its outer surface is reflected from the mirror according to the reflectivity of the coating, and no light is transmitted by the mirror. By that means, the mirror can be switched between a reflectivity level according to the reflectivity of the coating on the mirror, and a transmission level according to the complement of the reflectivity of the coating on the mirror.

When the mirror 20 is not activated and behaves as an optically transmissive element, or more accurately, as a partially transmissive element, the camera 13 images light coming from the lumen walls 15 ahead of the endoscope, as shown in FIG. 2A. That part of the light coming from the partial reflection of the rear field of view of the system can be subtracted, as previously described herewithin. When the mirror 20 is activated to prevent transmission, and to reflect the light from its outer layer, the camera 13 images light reflected from the proximal walls 16 of the lumen, and a backward view of the tissue is obtained, as shown in FIG. 2B. Using such an electronically or electrically activated mirror, the operator can see a forward or a backward view on-demand.

Figure 3A:
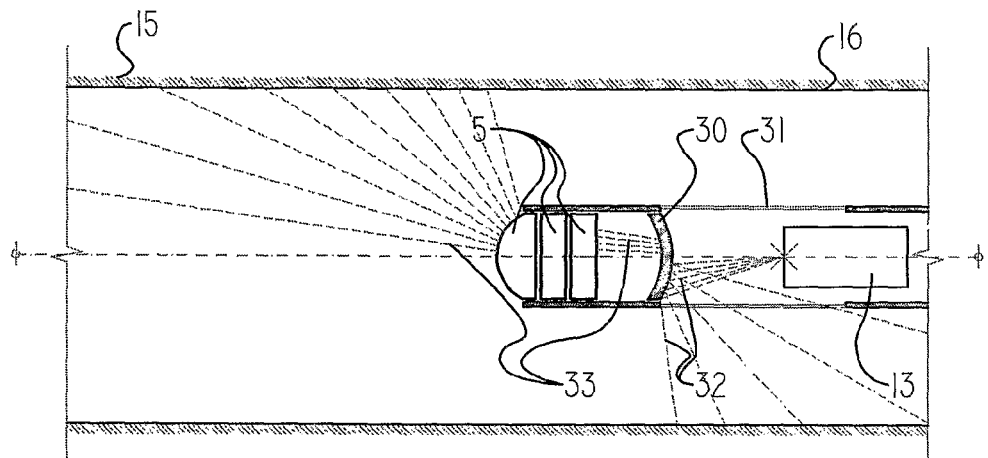
FIGS. 3A and 3B illustrate schematically a further exemplary endoscopic illumination system, in which the use of switchable transmissive material enables a front or rear view to be selectively obtained.
Figure 3B:
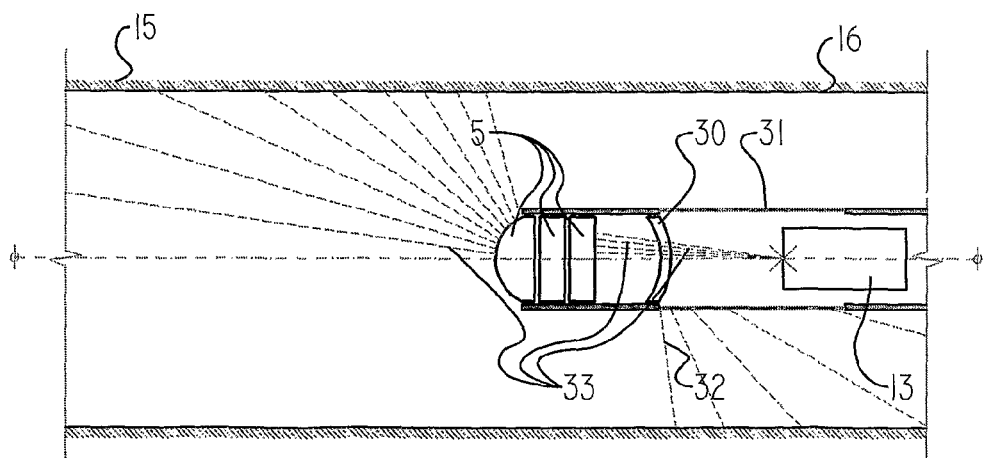

Reference is now made to FIGS. 3A and 3B, which illustrate schematically a further exemplary endoscopic illumination system, in which the use of switchable transmissive material enables a front or rear view to be selectively obtained. As previously mentioned, when working in a bodily lumen or cavity, reflection and scattering of light from the tissue of the wall occurs. Thus, when the system is in its front viewing mode, most of the light will be directed to the forward viewing field—but some illumination will be reflected to the back viewing field. In this case the mirror will reflect both the primary image front view (with 80% or 90% of the light intensity, for example) and a residual image back view (of a 20% or 10% intensity component, for example).

In order to resolve this issue in a different way, the system may be used in two different operational modes. The first mode is back view, in which the curved mirror material is activated to be opaque such that the mirror 30 is partially reflective, and the light can travel from the proximal lumen walls 16 to the camera sensor 13, as shown by illumination 32 reflected by the mirror 30. The second mode of operation is front view; in this mode of operation the curved semi mirror 30 is activated to be transparent, such that light 33 can travel both from the front of the endoscope, and from the sides 32. In such a case, two collinear images are formed. To prevent such superposition of the images, in the examples shown in FIGS. 3A, 3B, an optical boundary element such as a cylinder 31 is used between the endoscope distal end and the curved imaging switching mirror 30, the cylinder being constructed of an optically switchable material, such that it can change from transparent to opaque. When switched to be opaque, it blocks any illumination 32 coming from the lumen walls 16 in the back field of view, such that a clear front view only will be obtained. This system is thus able to generate a clear image with essentially switchable full front view and rear views, without mutually interfering secondary reflections.

In the example shown in FIGS. 3A and 3B, the optical boundary element 31 is shown as an extension of the endoscope outer cover, and the front lens assembly 5 of the camera may be attached to its distal end.

Figure 4A:
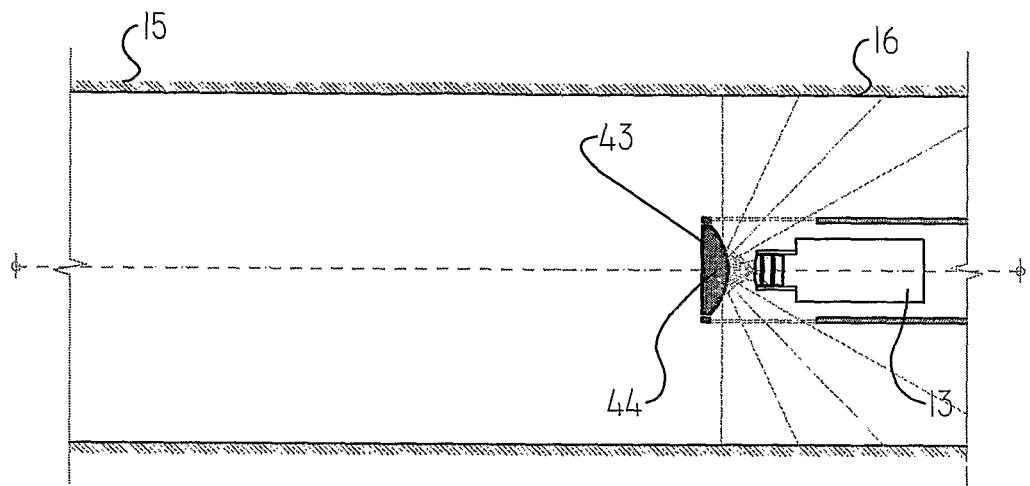
FIGS. 4A and 4B illustrate schematically another exemplary endoscopic illumination system using a fluid activated optical element for switching the forward and rearward views.
Figure 4B:
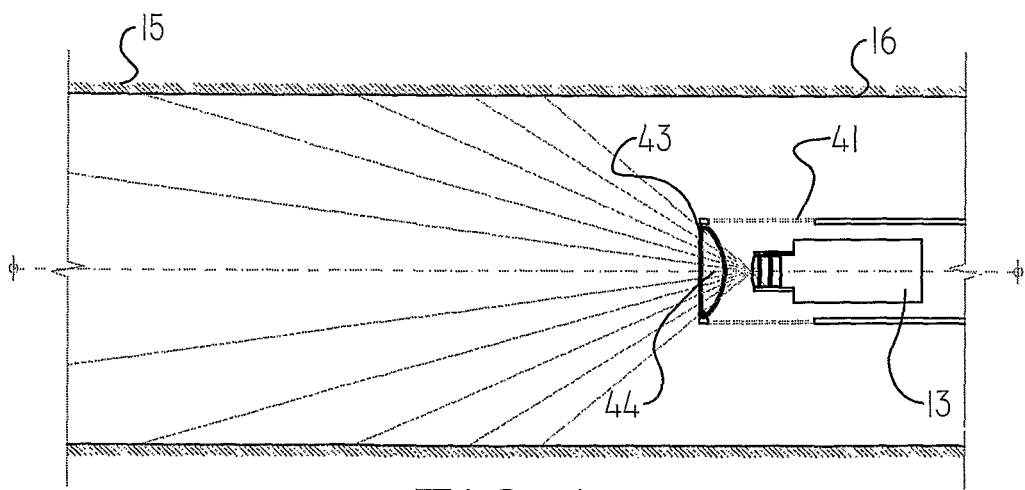

Reference is now made to FIGS. 4A and 4B, which illustrate schematically another exemplary endoscopic illumination system using a fluid activated optical element 43 for switching the forward and rearward views. The element 43 is in the form of a hollow container, which can be alternately filled with a reflective or transparent liquid 44. The rear surface of the container is shaped to have the profile of a convex mirror, such that when a reflective fluid, such as mercury, is injected into it, it will become a reflective mirror, directing the rear view of the lumen walls 16 into the camera, while if empty or filled with a transparent fluid, the front view wall 15 will be imaged by the camera. The operator can thus switch between forward and backward views on-demand. This could also be achieved by filling the container with fluid that can change its properties from reflective to transparent under the influence of an electrical field. As explained in the system shown in FIGS. 3A and 3B, the use of a switchable optical boundary element 41 can prevent rear illumination from interfering with the front view when the container is in its transparent state for front view imaging.

Figure 5A:
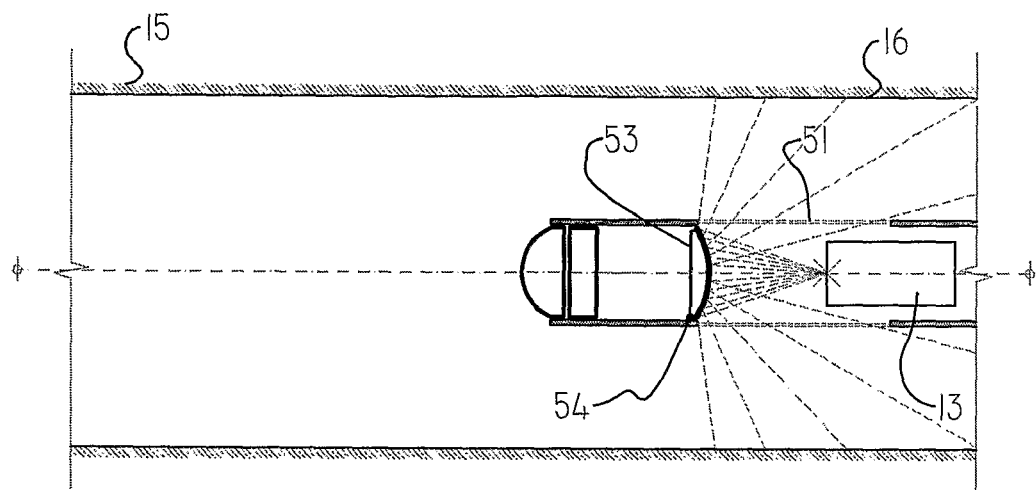
FIGS. 5A and 5B show schematically a further example of an endoscopic illumination system using a mechanically switchable mirror.
Figure 5B:
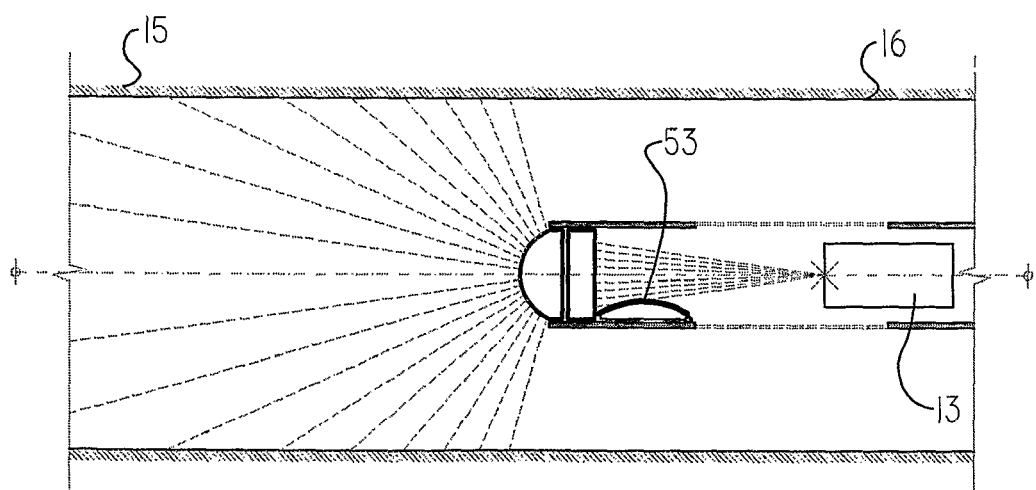

All of the above described examples have involved static systems, in that the illumination switching is performed without any need to move any optical elements. Reference is now made to FIGS. 5A and 5B, which show schematically a further example of an endoscopic illumination system using a mechanically switchable mirror 53. In FIG. 5A, the mirror is in its deployed position, imaging the rear view 16 into the camera. In FIG. 5B, the mirror activation mechanism has been operated to swing the mirror on its axis 54, so that the camera 13 can image the front view of the lumen walls 15. The mirror activation mechanism can be operated electrically or mechanically, enabling simple switching between forward and backward views.

Figure 6A:
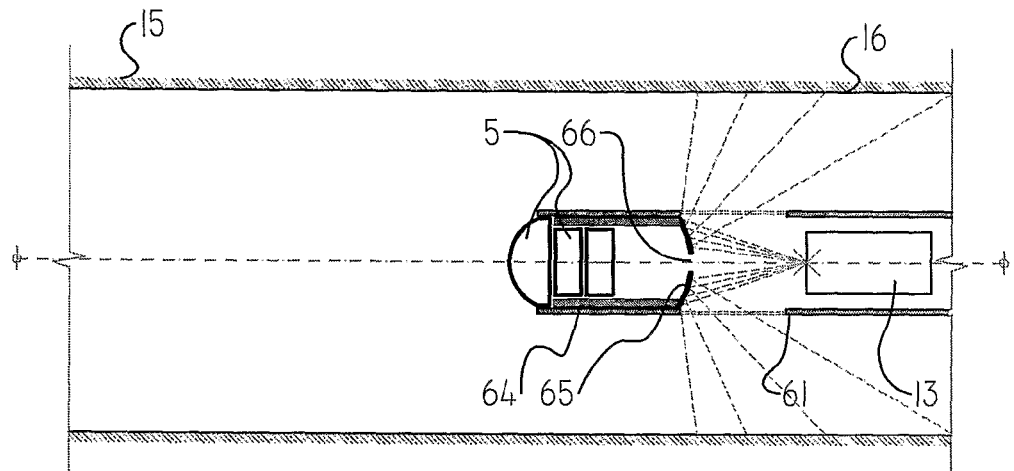
FIGS. 6A and 6B illustrate schematically a double view endoscopic system using a mechanically switched camera using linear motion of the reflection mirror.
Figure 6B:
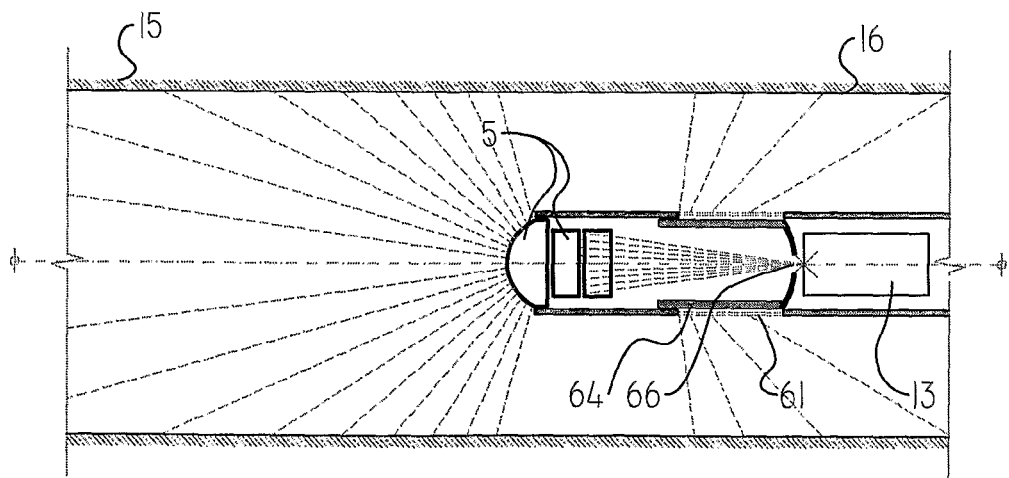

Reference is now made to FIGS. 6A and 6B, which illustrate schematically a double view endoscopic system using a mechanically switched camera using linear motion of the reflection mirror 65. The mirror 65 may be moved by virtue of it being mounted in a sliding bearing 64. The mirror has a small opening 66 at its center. When the mirror is moved to the front end of its travel as shown in FIG. 6A, whether mechanically, electronically or pneumatically, the camera 13 will image the backward view 16.

When the mirror 65 is moved backwards towards the camera, as shown in FIG. 6B, the light from the forward view walls 15 can pass through the hole 66 in the center of the mirror, and the camera 13 then has an unobstructed front view through the imaging lens set 5. Unlike the previous arrangements of FIGS. 4A, 4B, 5A and 5B, since the sliding bearing 64 of this implementation can be made of an opaque material, there is no need for the lens support barrel 61 to be optically switchable. When the front view is being imaged, as in FIG. 6B, the barrel 61 prevents ingress of light from the rear wall regions 16 into the front image illumination.

Figure 6C:
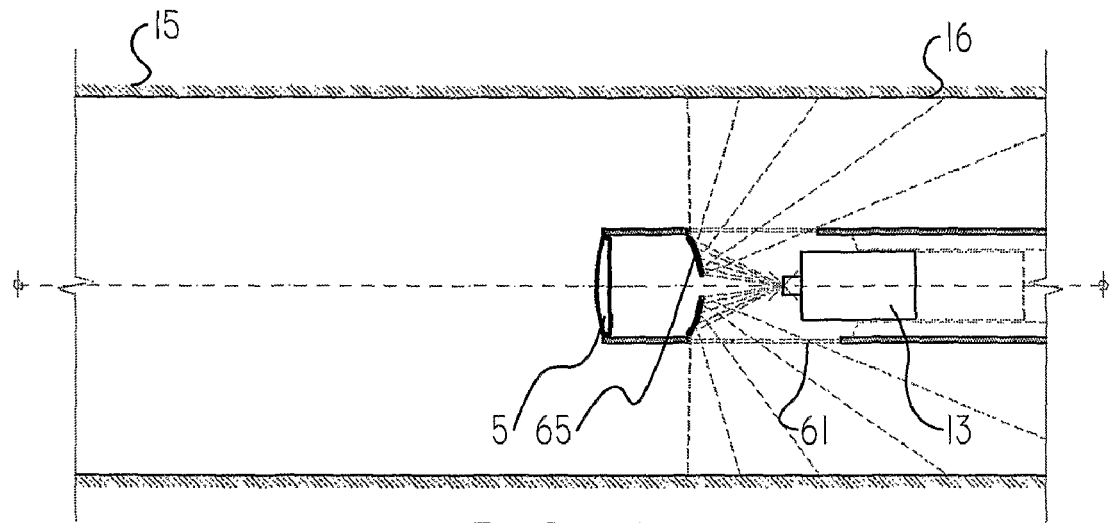
FIGS. 6C and 6D illustrate schematically a double view endoscopic system similar to that of FIGS. 6A and 6B, except that instead of moving the mirror back and forth, the camera can be moved back and forth, achieving similar results but with a stationary mirror.
Figure 6D:
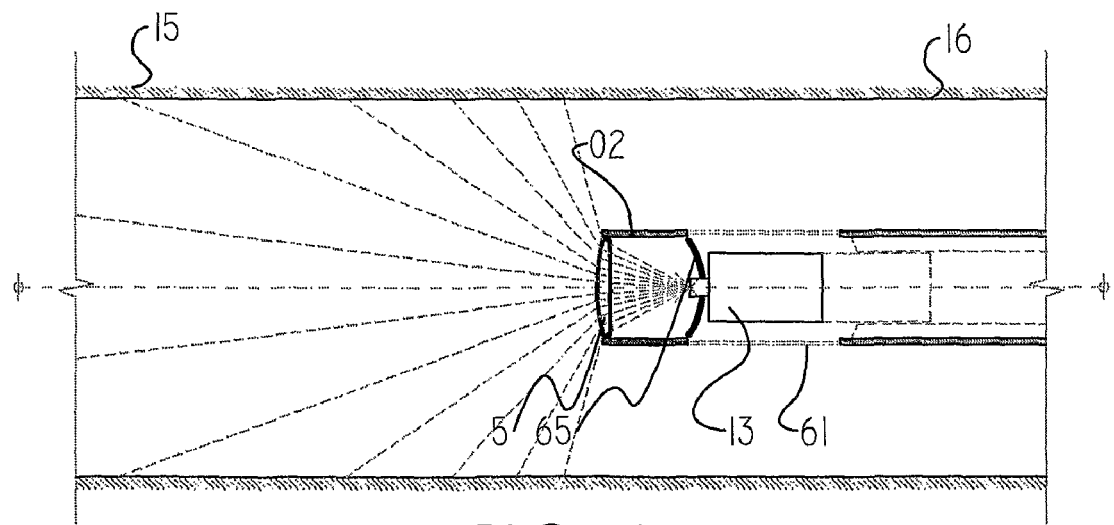

Reference is now made to FIGS. 6C and 6D, which show a similar arrangement to that of FIGS. 6A and 6B, with a mirror 65 with a central hole, except that in the case of FIGS. 6C and 6D, instead of moving the mirror back and forth, the camera 13 can be moved back and forth, achieving similar results but with a stationary mirror.

Figure 6E:
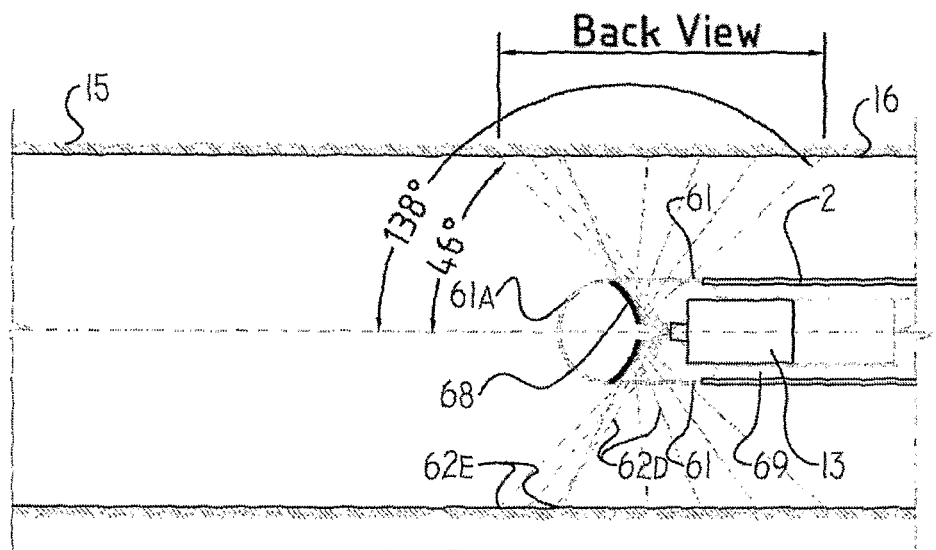
FIGS. 6E and 6F show schematically how the front view and the back view obtained by the systems of FIGS. 6A to 6D can overlap, such that a continuous view of the lumen being negotiated is obtained.
Figure 6F:
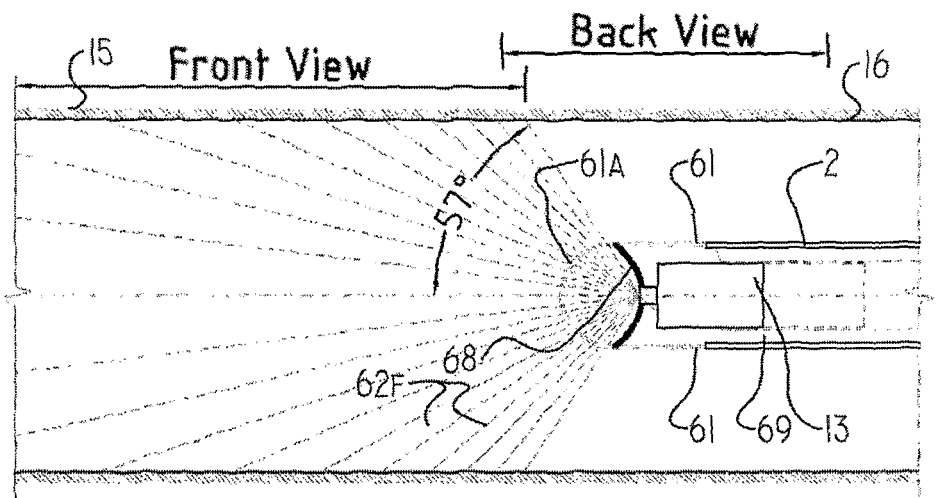

Reference is now made to FIGS. 6E and 6F, which show schematically how the front view and the back view obtained by the above described examples can overlap, such that a continuous view of the lumen being negotiated is obtained. The movable camera implementation of FIGS. 6C and 6D is used for illustrating this feature. In FIG. 6E, the camera 13 is shown in its proximal position, such that it images the wall 16 of the back part of the lumen. For the geometry shown in the rear view example of FIG. 6E, the angular span of the field of view, as defined by the imaging paths 62D, covers an angle of 46° from the axis of the camera/imaging system back to 138° from the axis of the camera/imaging system, where the field of view is limited by the obstruction of the edge of the endoscope housing 61. In FIG. 6F, the camera 13 is shown in its distal position, close to the mirror 68, such that it images the wall 15 of the forward part of the lumen. For the geometry shown in the forward view example of FIG. 6F, the angular span of the field of view, as defined by the imaging paths 62F covers an angle of ±57° from the axis of the camera/imaging system. There is thus a region between the angles 46° and 57° from the axis which is covered by both views, such that the illumination system does not leave any blind spots within the lumen not covered by the imaging system.

Figure 7A:
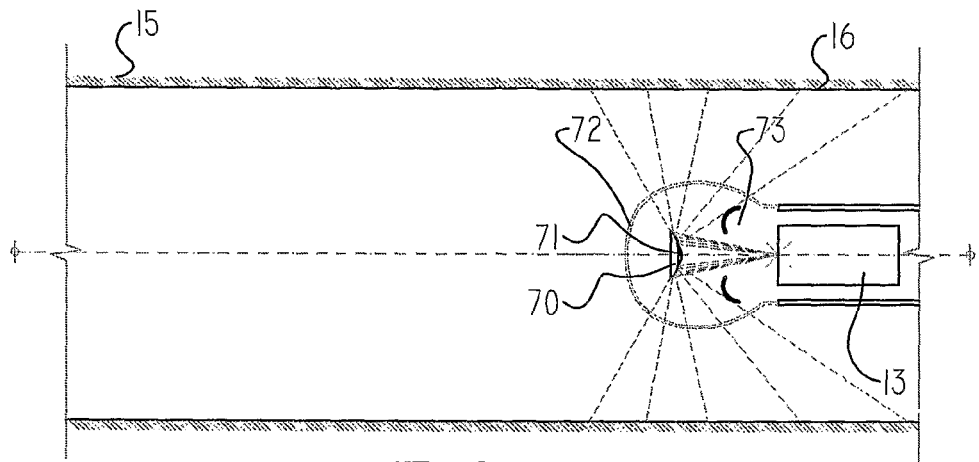
FIGS. 7A and 7B illustrate schematically a further exemplary endoscopic illumination system using a bi-radial convex mirror having surfaces each having a different radius of curvature, and a ring shaped mirror.
Figure 7B:
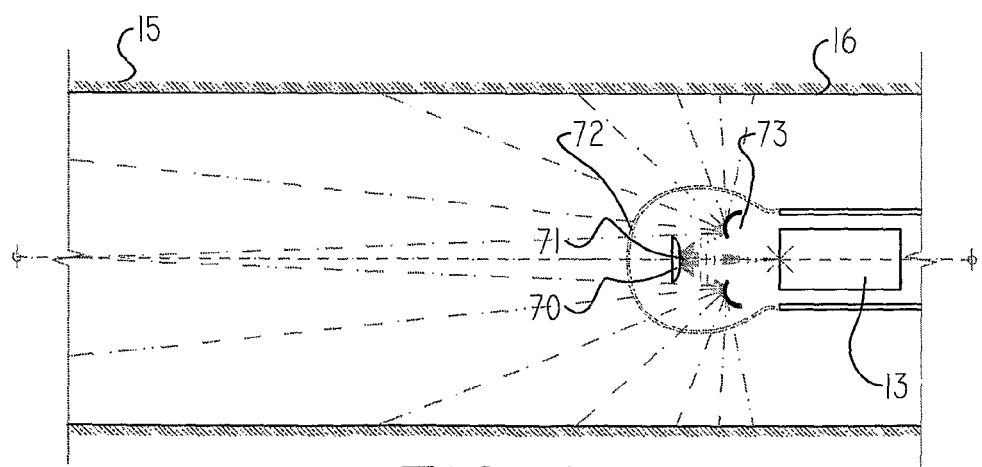

Reference is now made to FIGS. 7A and 7B, which illustrate schematically a further exemplary endoscopic illumination system enabling the generation of a combined front and rear view. The optical imaging system may be equipped with a convex mirror 70, and a ring shaped mirror 73. The light coming from the lumen walls 16 at the back side of the camera is reflected by the convex mirror 70 into the camera, thus giving the rear view.

Additionally, the light coming from the walls 15 at the front side is reflected by the ring mirror 73 onto the curved mirror 70, and then into the camera giving the front view. By using software stitching algorithms, as is known in the art, the front and backward views may be combined to obtain a complete front and rear view image. A transparent protective cover 72 is shown in these drawings, whose function is to prevent the entry of physiological debris onto the camera and lens.

In the example shown in FIGS. 7A and 7B, the convex mirror can advantageously be a full reflective mirror. Additionally, the ring mirror can be either a toroidal shaped convex mirror as shown in FIGS. 7A and 7B, or it may be a planar mirror, or even a concave toroidal mirror. Furthermore, the mirror 70 has to fulfill two different focusing functions:
(i) to direct the light coming directly from the rearward surface 16 of the lumen into the imaging device 13, and
(ii) to direct the light coming from the forward surface 15 of the lumen into the imaging device 13, after reflection in the ring mirror 73.
Therefore, the main mirror 70 may be advantageously provided with two separate concentric regions, each having a surface with a different radius of curvature, such that each region performs its focusing function effectively. This is shown in FIGS. 7A and 7B, where the outer main section of the mirror 70 has one radius of curvature, and the inner region of the mirror 71, has a second radius of curvature, providing a different optical power.

Furthermore, although the ring mirror 73 is shown in FIGS. 7A and 7B located between the main mirror 70, 71 and the imaging device 13, it is to be understood that it can even be located rearward of the imaging device, so long as its position and optical power enable it to image the light coming from the parts of the forward walls of the lumen desired to be viewed onto the main mirror 70, 71 and into the imaging device.

One of the problems of endoscopic illumination systems arises from lack of uniformity of illumination of the lumen being inspected. In particular, movement of the endoscope away from the centerline of the lumen can result in greatly increased illumination on one wall closer to the illumination source, and reduced illumination on the opposite wall, possible leading to difficulties in the correct interpretation of the images obtained.

Reference is now made to FIGS. 8A to 8E which illustrate an endoscope system equipped with multiple illumination sources arranged around the periphery of the endoscope head. The endoscope can be of a similar type to those described hereinabove, with a camera 13, a lens system 5, and a protective sleeve 81. The illumination control circuits are arranged such that the illumination level from each source or group of sources can be independently controlled to counteract non-uniform illumination effects. Each section of the surrounding tissue can thus be selectively illuminated at a different light intensity, in order to generate uniform illumination on the lumen walls. The illumination can either be controlled manually by the user to obtain the most uniform illumination perception, or it can be controlled automatically by a feedback system based on photometric sensors 85 detecting the illumination levels at various circumferential positions on the lumen wall.

FIGS. 8A and 8B show the situation when the endoscope is located in the center of the lumen. The illumination 81A and 81D, as shown in FIG. 8A is equally distributed on the walls of the lumen 15, 16. When the endoscope is moved closer to one side of the lumen wall, as shown in FIGS. 8C and 8D, the light sources closer to the wall will illuminate the wall more strongly 81B than those further away from the wall 81C. In order to equalize the wall illumination, the light sources are driven such that the sources closer to the wall emit less light, and those further from the walls have increased light intensity. By this means, a radial illumination balance is obtained.

Reference is now made to FIG. 8E, which illustrates schematically a simple arrangement for achieving control of the uniformity of the illumination. The feedback system can conveniently be based on an external controller 87 receiving its inputs from the photo-detectors 85 by wiring running back through the endoscope tubing, and instructing the illumination source power supply 88 to deliver the accordingly controlled power for the illumination sources back along multiple wires. In FIG. 8E, for simplicity, only a single wire connection is shown for a single photo-detector 85 and a single illumination source 80, though it is to be understood that each of these elements generally requires its own connecting wire. The controller 87 is programmed such that when a photo-detector in a certain radial sector detects a reduction in lumen wall illumination, the current drive to the illumination sources in that sector is increased to compensate for the reduction in illumination, until the control loop has locked the illumination back at its initial reference level. The converse happens if a photo-detector detects that the illumination is rising. This arrangement is only one manner by which such control can be accomplished, and other arrangements may be equally well used. For instance, communication with the control system can also be achieved wirelessly, or a self-powered controller can be carried on-board the endoscope head.

Another method by which control of the spatial spread of the illumination can be achieved is by analysis of the intensity levels within the images obtained by the camera, and use of the results of such analysis to control the illumination source outputs.

Figure 9A:
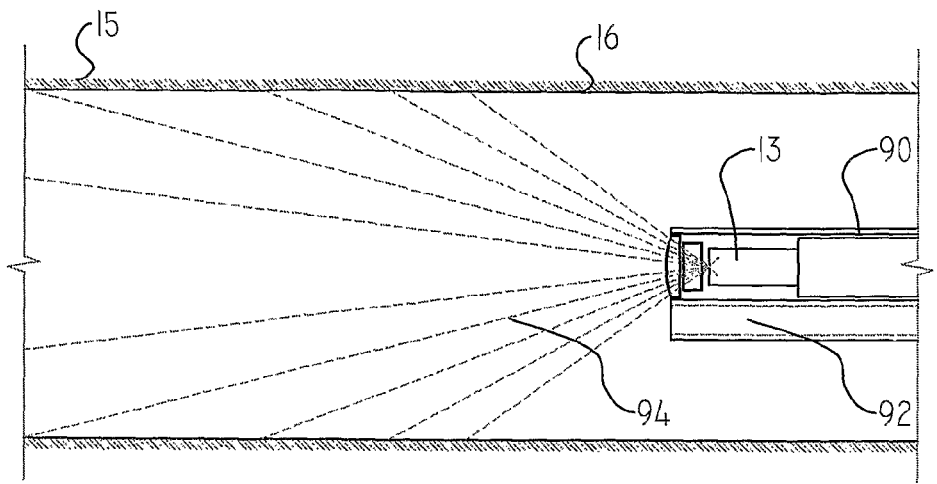
FIGS. 9A, 9B and 9C schematically illustrate a further exemplary implementation of an endoscopic illumination system, using an inflatable rear view mirror in the form of an inflatable reflective balloon.
Figure 9B:
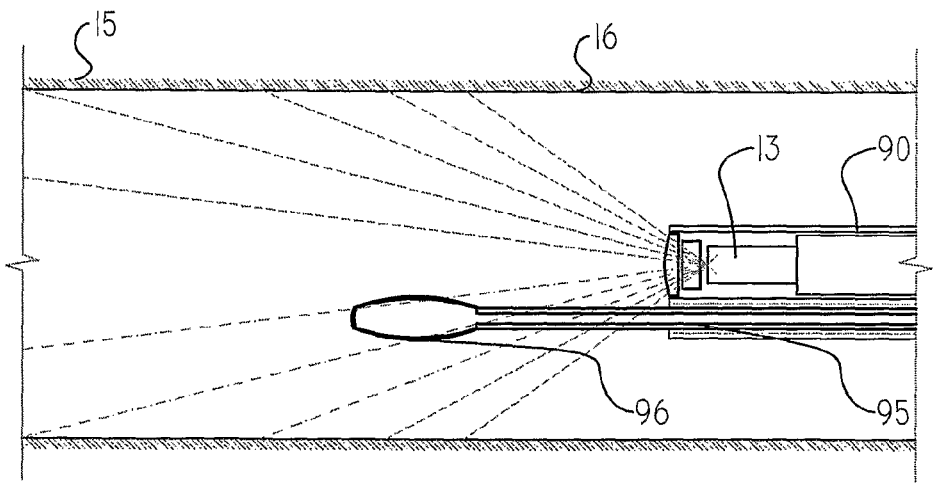
Figure 9C:
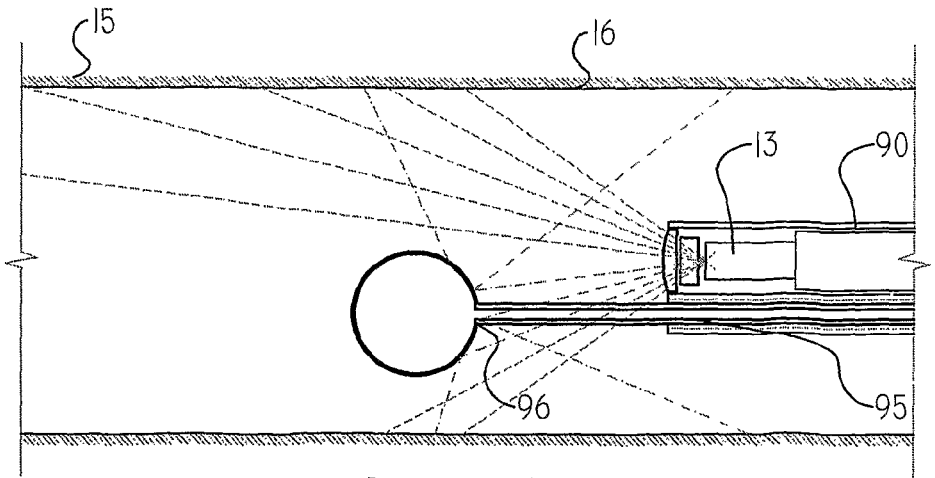

Reference is now made to FIGS. 9A, 9B and 9C, which schematically illustrate a further exemplary implementation of an endoscopic illumination system, whereby the light emanating from the walls 16 rearward of the endoscope camera illumination is reflected into the camera by means of an inflatable rear view mirror in the form of an inflatable reflective balloon. FIG. 9A shows the endoscope body 90, with the camera 13 and a working channel 92. The illumination 94 coming from the forward walls 15 of the lumen enter the camera 13 in the normal manner. FIG. 9B shows the deployment from the working channel 92 of an inflatable reflective balloon 96 with its inflation tube 95. FIG. 9C shows the inflatable reflective balloon fully inflated and deployed in a predetermined position that ensures that illumination from the back side 16 of the endoscope is reflected into the camera lens. The balloon mirror should have a predetermined spherical, parabolic or other shape, calculated to ensure correct focusing of the rearward originating illumination into the camera.

During body lumen inspection the front view is obtained in the normal manner using the front-viewing camera. The inflatable mirror can be introduced on-demand to obtain a rear view of the lumen without the need to steer the endoscope backward, allowing thorough inspection in limited space and using an existing endoscope. The inflatable mirror device can be made disposable.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for viewing the inside surface of a lumen, said system comprising:
    an imaging device directed along said lumen; and
    a mirror disposed distal to said imaging device, said mirror comprising a central aperture, and being mutually movable in a direction along said lumen, such that when said imaging device is disposed at a predetermined distance from said mirror, said imaging device images said inside surface of said lumen proximal to said mirror, and when said imaging device is disposed close to said mirror, said imaging device images, through said aperture, said inside surface of said lumen distal to said mirror.

2. A system according to claim 1, wherein at least one of said imaging device and said mirror are moveable relative to the other.

3. A system according to claim 1, wherein said mirror is moveable relative to a static imaging device.

4. A system according to claim 1, wherein said both said mirror and said imaging device are moveable.

5. A system according to claim 1, wherein said mirror is a convex mirror.

\* \* \* \* \*